(12) United States Patent
Volckens et al.

(10) Patent No.: US 8,973,447 B2
(45) Date of Patent: Mar. 10, 2015

(54) THERMOPHORETIC SAMPLER

(75) Inventors: John Volckens, Fort Collins, CO (US); Gary Casuccio, Brave, PA (US); Henry P. Lentz, Apache Junction, AZ (US); Anthony Marchese, Fort Collins, CO (US); John T. Mastovich, Murrysville, PA (US); Daniel David Miller-Lionberg, Fort Collins, CO (US); Judith Chun-Hsu Yang, Pittsburgh, PA (US)

(73) Assignee: Colorado State University Research Foundation, Fort Collins, CO (US)

( * ) Notice: Subject to any disclaimer, the term of this patent is extended or adjusted under 35 U.S.C. 154(b) by 267 days.

(21) Appl. No.: 13/480,322

(22) Filed: May 24, 2012

(65) Prior Publication Data
US 2013/0133441 A1 May 30, 2013

Related U.S. Application Data

(60) Provisional application No. 61/489,598, filed on May 24, 2011.

(51) Int. Cl.
*G01N 1/22* (2006.01)
*G01N 1/02* (2006.01)
*G01N 15/00* (2006.01)

(52) U.S. Cl.
CPC .............. *G01N 1/02* (2013.01); *G01N 1/2202* (2013.01); *G01N 2001/2276* (2013.01); *G01N 2015/0038* (2013.01)
USPC .................................... 73/863.22; 73/863.12

(58) Field of Classification Search
CPC .......................... G01N 1/2202; G01N 1/2208
See application file for complete search history.

(56) References Cited

U.S. PATENT DOCUMENTS 6,666,905 B2 * 12/2003 Page et al. ............................ 95/1
2012/0175289 A1 * 7/2012 Bystron et al. .................. 210/91

OTHER PUBLICATIONS

Lorenzo et al., "A Thermophoretic Precipitator for the Representative Collection of Atmospheric Ultrafine Particles for Microscopic Analysis", Aerosol Science and Technology, 41(10): 934-943, 2007.*
Gonzalez, David et al. (2005) "A New Thermophoretic Precipitator for Collection of Nanometer-Sized Aerosol Particles," Aerosol Science and Technology, 39:1064-1071.*
Azong-Wara, N. et al., Optimisation of a thermophoretic personal sampler for nanoparticle exposure studies, J Nanopart Res (2009) 11:1611-1624.
Gonzalez, D. et al., A New Thermophoretic Precipitator for Collection of Nanometer-Sized Aerosol Particles, Aerosol Science and Technology (2005) 39:1064-1071.
Miller, A. et al., A Handheld Electrostatic Precipitator for Sampling Airborne Particles and Nanoparticles, Aerosol Science and Technology (Apr. 20, 2010) 44:6, 417-427.

(Continued)

*Primary Examiner* — Paul West
(74) *Attorney, Agent, or Firm* — Faegre Baker Daniels LLP (57) ABSTRACT

A thermophoretic sampler includes a sample assembly into which a removable sample cartridge can be inserted. The sample cartridge holds a substrate that, upon insertion, is exposed to a sample chamber. Thermophoresis is induced in the sample chamber, causing nanoparticles to be deposited on the substrate.

14 Claims, 7 Drawing Sheets

(56) References Cited

OTHER PUBLICATIONS

Miller, A. et al., Design Optimization of a Portable Thermophoretic Precipitator Nanoparticle Sampler, Aerosol Science and Technology (2012) 46:8, 897-904.

Peters, T.M. et al. Impactors, Cyclones, and Other Particle Collectors, American Conference of Governmental Industrial Hygienists (ACGIH) (2008), pp. 1-39.

\* cited by examiner

THERMOPHORETIC SAMPLER

CROSS-REFERENCE TO RELATED APPLICATIONS

This application claims priority to U.S. Provisional Application No. 61/489,598, filed May 24, 2011, and entitled "Personal, Thermophoretic Sampler for Airborne Nanoparticles," the entirety of which is incorporated herein by reference.

STATEMENT REGARDING FEDERALLY SPONSORED RESEARCH OR DEVELOPMENT

This invention was made with government support under Grant No. R03 OH009381 awarded by the Centers for Disease Control. The government has certain rights in the invention.

BACKGROUND

Advances in the nanotechnology industry and related economic rewards are being questioned from the perspective of potential health effects associated with exposure to nanomaterials. Some suspect the slowing of the financial investment in nanotechnology may be related to the potential health risks. Higher quality health risk assessments can be facilitated by capturing engineered nanoparticles and differentiating them from naturally occurring counterparts.

As the nanotechnology industry expands, there is growing concern among scientists, policymakers, and consumers regarding the health and safety impacts that nanomaterial proliferation may exert on humans and the environment. For example, if a certain nanomaterial exhibits altered physiochemical behavior, it may also exert unknown and unpredicted effects within the environment or the human body. While the debate regarding such effects has yet to be resolved scientifically, there is some evidence supporting the increased toxicity of nanoscale materials. Additional concerns with nanoparticles include their ability to cross tissue barriers and translocate to different areas of the body. For example, inhaled nanoparticles have been shown to undergo extrapulmonary translocation into the systemic circulation, with subsequent deposition in peripheral tissues.

Methods for nanoparticle speciation are useful because biogenic (e.g., sea salt) and anthropogenic (e.g., diesel soot) nanoparticles often outnumber airborne concentrations of engineered nanoparticles, even in locations where engineered nanoparticles are being produced and handled. Consequently, an exposure assessment that distinguishes engineered nanomaterials from biogenic and incidental nanoparticles can be useful, especially if the goal is to investigate environmental health and safety impacts resulting from exposure. Current nanoparticle measurement methods using only direct reading instruments (DRI) typically do not include nanoparticle identification.

SUMMARY

Embodiments of the disclosed subject matter include a miniaturized thermophoretic sampler. Embodiments of the thermophoretic sampler permit collection of nanoparticles that can be speciated using analytical techniques. Embodiments of the sampler can collect nanoparticles from a person's breathing zone to facilitate worker exposure and risk assessment studies.

While multiple embodiments are disclosed, still other embodiments of the subject matter will become apparent to those skilled in the art from the following detailed description, which shows and describes illustrative embodiments of the subject matter. Accordingly, the drawings and detailed description are to be regarded as illustrative in nature and not restrictive.

While embodiments of the disclosed subject matter are amenable to various modifications and alternative forms, specific embodiments have been shown by way of example in the drawings and are described in detail below. The intention, however, is not to limit the subject matter to the particular embodiments described. On the contrary, the subject matter is intended to cover all modifications, equivalents, and alternatives falling within the scope of the disclosure as defined by the appended claims.

DETAILED DESCRIPTION

Embodiments of the thermophoretic sampler collect airborne particles by applying a temperature gradient to a sample chamber that defines a portion of an air flow. Because of the temperature gradient (e.g., ~100° C./mm from the top to the bottom of the sample chamber), gas molecules on one side of a particle have greater kinetic energy than those on the opposite side. Molecules on the hotter side transfer more net momentum per collision to the particle, resulting in a thermophoretic force. The movement of a particle in the direction of decreasing temperature, called its thermophoretic velocity, will eventually cause the particle to deposit onto a substrate.

In embodiments, a miniaturized thermophoretic sampler provides the capability of capturing airborne nanoparticles via thermophoretic force directly onto a transmission electron microscope (TEM) substrate. In embodiments, different types of substrates can be used to enable capture and subsequent analyses of nanoparticles in various analytical instruments and related techniques such as, for example, excitation tools including electron-ion (e.g., SEM, EMPA, etc.), x-ray (e.g., XPS, XRF, XRD, etc.), laser/light (e.g., Raman, LICP, FTIR, PLM, etc.), and the like. Additionally, embodiments include combining a thermophoretic sampler with other nanoparticle measurement devices such as, for example, direct reading instruments (DRIs), biosensors, gas detectors, nanoparticle sizers, particle counters, and the like.

Figures 1A, 1B, 1C, 1D, 1E:
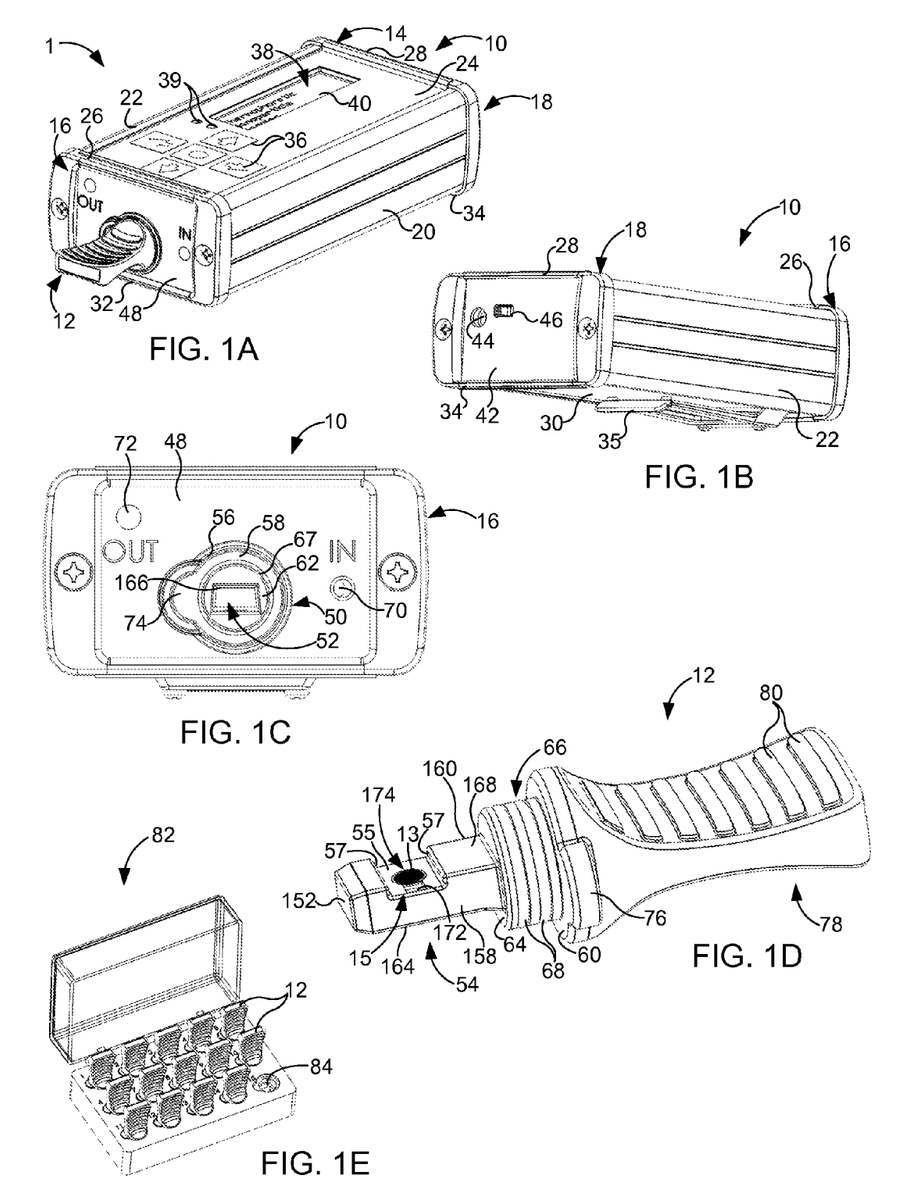
FIGS. 1A and 1B are perspective views of a thermophoretic sampler in accordance with embodiments of the disclosure.
FIG. 1C is a front view of the thermophoretic sampler of FIGS. 1A and 1B in accordance with embodiments of the disclosure.
FIG. 1D is a perspective view of a sample cartridge in accordance with embodiments of the disclosure.
FIG. 1E is a perspective view of a sample cartridge carrying case in accordance with embodiments of the disclosure.

FIGS. 1A-1H depict an illustrative personal thermophoretic sampler 1. In embodiments, the sampler 1 can be worn or carried by a user to facilitate collection of nanoparticles from the user's environment such as, for example, in a region corresponding to air that the user breaths. The sampler 1 includes a sampler assembly 10 and a removable sample cartridge 12 to which a substrate 13 can be removably coupled. According to embodiments, when the cartridge 12 is inserted in the sampler assembly 10, the substrate 13 is exposed to a sample chamber 117 (illustrated in FIGS. 2A and 2B) and thermophoresis causes nanoparticles to be deposited on the substrate 13. According to embodiments, the substrate 13 can be a transmission electron microscopy grid, a thin foil substrate, or the like. As shown in FIGS. 1A and 1B, the sampler assembly 10 includes a housing 14 having a front frame 16, a rear frame 18 and a pair of opposed side walls 20 and 22, extending between the front and rear frames 16 and 18. A top plate 24 extends between a top edge 26 of the front frame 16 and a top edge 28 of the rear frame 18 and a bottom plate 30 extends between a bottom edge 32 of the front frame 16 and a bottom edge 34 of the rear frame 18. As shown in FIG. 1, the housing 14 has a generally rectangular shape, although in embodiments, any number of other configurations can be used for the housing 14. In embodiments, as illustrated, the housing 14 can include a clip 35 that is coupled, for example, to the bottom plate 30 and that can be used to clip the sampler 1 to an article of clothing. In some embodiments, the housing 14 can include other mechanisms for facilitating wearing of the sampler 1 by a user such as, for example, a strap, a hook-and-loop system (e.g., Velcro®), or the like.

In embodiments, the top plate 24 and/or any number of other surfaces of the housing 14, can include any number of input devices 36 such as, for example, buttons, a touch-screen, switches, roller, slider, and the like. In the illustrated embodiment, the top plate 24 includes an aperture 38 that serves as a window through which a display 40 device can be viewed. In embodiments, the display device 40 can be, for example, an LCD screen, an LED screen, one or more LED lights, a touch-screen, or the like. As shown, the top plate 24 includes apertures 39 through which LED indicator lights 41 can be viewed. In embodiments, for example, the LED indicator lights 41 can be used to indicate whether the sampler 1 is powered on or off.

As shown in FIG. 1B, the housing 14 includes a rear plate 42 held in place by the rear frame 18. The rear plate 42 includes an aperture 44 for receiving a charging plug (not shown) and a switch 46 for powering up the sampler 1. In embodiments, other input/output jacks, switches, or the like can be included on the rear plate 42 (and/or, in embodiments, on other surfaces defining the housing 14).

As shown in FIGS. 1A and 1C, the housing 14 includes a front plate 48 held in place by the front frame 16. In the illustrated embodiment, the front plate 48 includes a cartridge port 50 for receiving the sample cartridge 12. As shown, a cartridge channel 52 extends from the cartridge port 50 into the sampler assembly 10 and is configured for receiving a first portion 54 of the sample cartridge 12, which includes the substrate 13. In the illustrated embodiment, the cartridge channel 52 has a generally trapezoidal shape, which corresponds to a generally trapezoidal shape of the first portion 54 of the sample cartridge. According to embodiments, using a shape that is asymmetrical with respect to at least one plane can facilitate proper insertion of the cartridge 12. For instance, in the illustrated embodiment, the trapezoidal shape of the cartridge 12 and the corresponding cartridge channel 52 can prevent a user from inserting the cartridge 12 upside-down, in which case the substrate 13 would not be exposed to the sample chamber In other embodiments, the cartridge channel 52 and the first portion 54 of the cartridge can be configured according to other shapes, depending on the details of the implementation, such as, for example, rectangular shapes, circular shapes, triangular shapes, pentagonal shapes, and the like.

As shown, the cartridge port 50 includes a first surface 56 extending from the front plate 48 to a first stopping surface 58, which may lie in a plane substantially parallel to the front plate 48. According to embodiments, when the sample cartridge 12 is fully inserted through the cartridge port 50, the first stopping surface 58 engages a surface 60 on the sample cartridge 12 and a second stopping surface 62, defined within the cartridge port 50, engages a second surface 64 on the sample cartridge. In this fully inserted position, a sealing portion 66 of the sample cartridge 12 engages a second surface 67 of the cartridge port 50 to create a seal from the outside environment. In embodiments, as shown in FIG. 1D, the sealing portion 66 of the sample cartridge 12 includes one or more sealing mechanisms 68 such as, for example, o-rings, gaskets, or the like. In embodiments, the second surface 67 can be ribbed or otherwise contoured to facilitate the sealing action of the sealing mechanisms 68. When the sample cartridge 12 is fully inserted, thereby causing the cartridge port 50 to be sealed from the outside environment, air enters and exits the sampler assembly 10 through an air inlet 70 and an air outlet 72, respectively. In embodiments, as shown in FIG. 1C, the air inlet 70 and outlet 72 can be defined in the front plate 48, while, in other embodiments, the air inlet 70 and air outlet 72 can be defined in other surfaces of the housing 14.

In embodiments, as shown in FIGS. 1C and 1D, the cartridge port 50 can include a guide feature 74 that corresponds to a protrusion 76 on the sample cartridge 12 to facilitate proper orientation when inserting the sample cartridge 12. Additionally, the sample cartridge 12 can include a handle portion 78 that can be gripped by a user for facilitating insertion and removal of the sample cartridge. In embodiments, the handle portion 78 can include any number of various types of grip features 80 to facilitate gripping by a user. In embodiments, the handle portion 78 may include low thermal conductivity plastic, whereas the first portion 54 may include high thermal-conductivity materials, which may maximize heat flow to the sample chamber (not shown) while minimizing heat flow to the surrounding enclosure. Additionally, in embodiments, the sampler 1 may be accompanied by a carrying case 82 that can be used to carry a number of sample cartridges 12. In embodiments, a number of different samples may be collected using different cartridges 12, which can be stored in the case 82 and transported to a destination for analysis. According to embodiments, the case 82 can include any number of slots 84 for holding cartridges and can be configured according to any number of different designs. In embodiments, the case 82 is configured to be sealed when it is closed, thereby facilitating avoiding exposure of the sample cartridges to contamination.

Figure 1F:
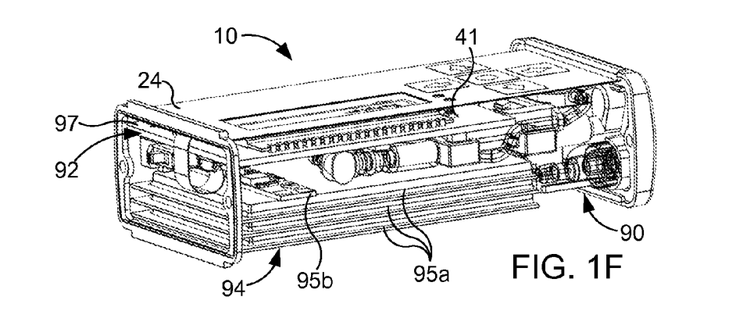
FIG. 1F is an internal perspective view of the thermophoretic sampler of FIGS. 1A and 1B in accordance with embodiments of the disclosure.
Figure 1G:
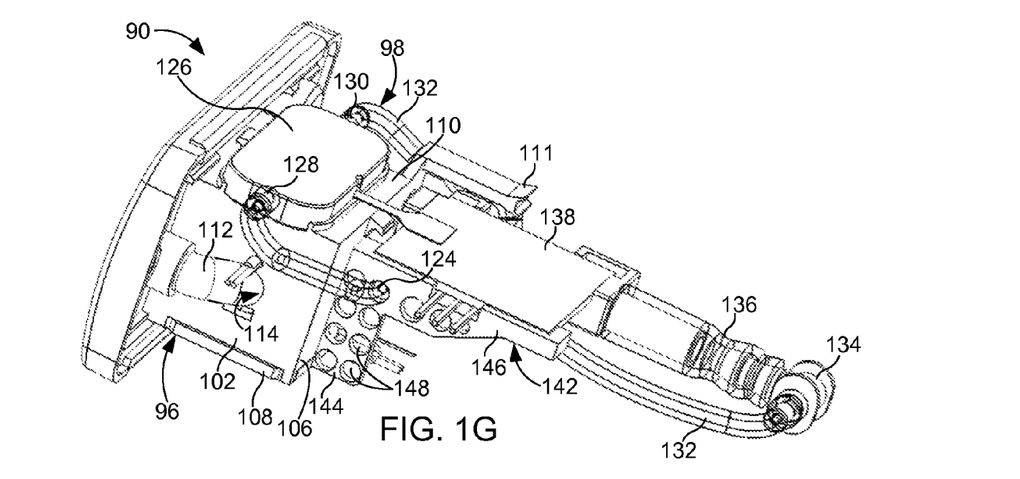
FIGS. 1G and 1H are perspective views of a sample core assembly in accordance with embodiments of the disclosure.

FIGS. 1F and 1G show internal views of the illustrative sampler assembly 10. As shown, the sampler assembly 10 includes a sample core assembly 90, a controller 92, and a battery assembly 94. According to embodiments, the controller 92 can include a microcontroller, a central processing unit (CPU), a programmable logic device (PLD), software, hardware, firmware, or any combination these and/or other components. The controller 92, as well as other electrical components of the sampler assembly 10, is powered by the battery assembly 94. In embodiments, the battery assembly 94 can include rechargeable battery cells 95a, a battery cell protection circuit 95b, and the like. The battery cells 95a can include, for example, lithium ion battery cells. In embodiments, the components 90, 92, and 94 can be configured within the housing 14 in any number of different arrangements.

Figure 1H:
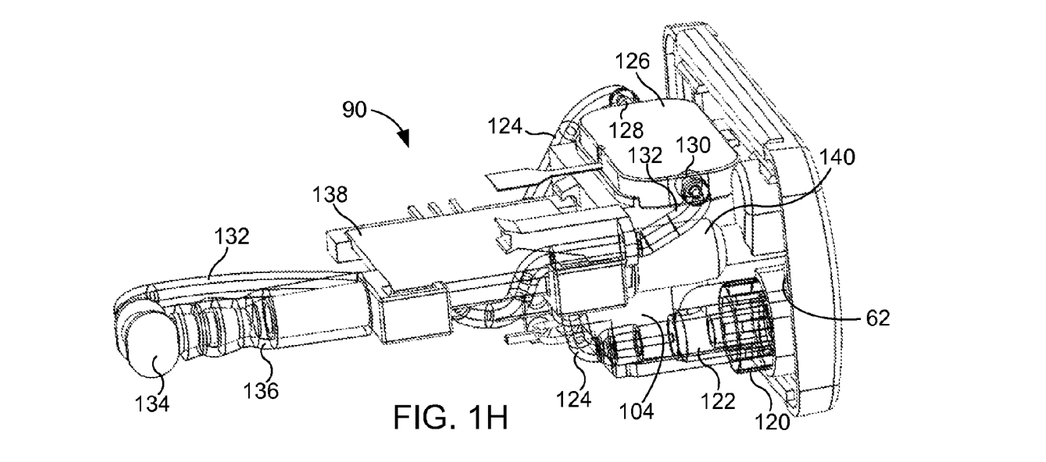

As depicted in FIG. 1G, the sample core assembly 90 includes a sample chamber housing 96 and an air flow assembly 98. The sample chamber housing 96 includes side walls 102 and 104, a rear wall 106, a front wall 62 (as shown in FIG. 1C), a lower wall 108, and an upper wall 110. Additionally, as shown in FIGS. 1F-1H, a stopping arm 111 can be mounted to the sample core assembly 90 for holding in place a printed circuit board (PCB) 97, which is a component of the controller 92.

The air flow assembly 98 provides a portion of an air flow path through the sampler assembly 10. According to embodiments, any number of different types of air flow assemblies can be used to facilitate moving air through the sample chamber housing 96. In the illustrated embodiments, the air flow assembly 98 includes an inlet duct 112 that extends from the air inlet 70 to an aperture 114 defined in the side wall 102 of the sample chamber assembly 96. The air flow assembly 98 further includes a filter base 120 to which a filter 122 is coupled. In embodiments, the filter base 120 can be integral with a front wall 62, mounted to the front wall 62, mounted to the sample chamber assembly 96, or the like. Filter-pump tubing 124 extends from the filter 122 to a pump 126. In embodiments, the pump 126 provides the fluid motion of the air through the assembly 10 and can comprise any number of different types of pumps such as, for example, a micropump. In embodiments, the pump 126 is communicatively coupled to the controller 92, which controls the operation of the pump 126.

As shown, the air flow assembly 98 further includes pump-elbow tubing 132 that extends from a pump outlet 128 to a reduction elbow 134, and elbow-flow sensor tubing 136 that extends from the reduction elbow 134 to a flow sensor 138. In embodiments, the flow sensor 138 can be any type of mass flow sensor that measures the amount of air passing through the sensor 138. According to embodiments, the flow sensor 138 can be coupled to the sample chamber housing 96 via a sensor mount 142. In the illustrated embodiment, the sensor mount 142 is generally L-shaped, having a first portion 144 coupled to the rear wall 106 of the sample chamber housing 96 and a second portion 146, extending away from the sample chamber housing 96. The mass flow sensor 138 is coupled to the second portion 146 of the sensor mount 142. In embodiments, one or both of the portions 144 and 146 of the sensor mount 142 can include apertures 148 through which tubing can be passed. In embodiments, other types of mounts or attachment mechanisms can be used to dispose the flow sensor 138 within the housing 14. Additionally, in embodiments, the flow sensor 138 is communicatively coupled to the controller 92 and provides flow measurements to the controller 92. A sensor output 140 extends from the flow sensor 138 to the air outlet 72 (depicted in FIG. 1C).

According to embodiments, the air flow assembly 98 and portions of the sample chamber assembly 96 define an air flow path, as follows. In the illustrated embodiment, air enters the sampler assembly 10 through the air inlet 70 and flows through an inlet duct 112 into the sample chamber housing 96 via an aperture 114 defined in the side wall 102. The air enters the sample chamber 117 (shown in FIGS. 2A and 2B) through a first internal duct 116 (shown in FIGS. 2A and 2B) and exits the sample chamber 117 into a second internal duct 118 (shown in FIGS. 2A and 2B), which directs the air through the filter base 120 and into the filter 122. The air exits the filter 122 into the filter-pump tubing 124 and moves through the filter-pump tubing 124 and into the pump 126 via a pump inlet 128. In embodiments, the pump 126 provides the fluid motion of the air through the assembly 10. The air exits the pump 126 via a pump outlet 130 and travels through the pump-elbow tubing 132, through the reduction elbow 134 and into the elbow-flow sensor tubing 136. The elbow-flow sensor tubing 136 directs the air into the flow sensor 138. The air exits the flow sensor 138 through the flow sensor output 140 and is expelled into the ambient environment through the air outlet 72 (depicted in FIG. 1C).

Figure 2A:
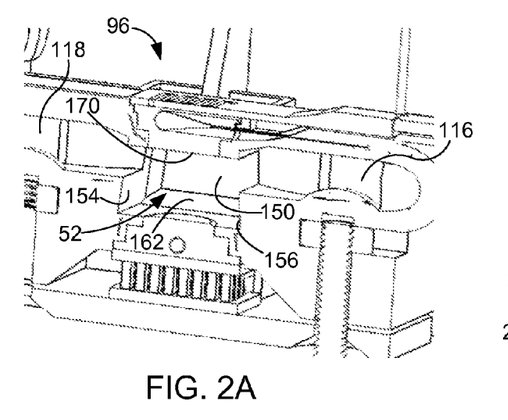
FIGS. 2A and 2B are cross-sectional perspective views of the thermophoretic sampler of FIGS. 1A and 1B in accordance with embodiments of the disclosure.
Figure 2B:
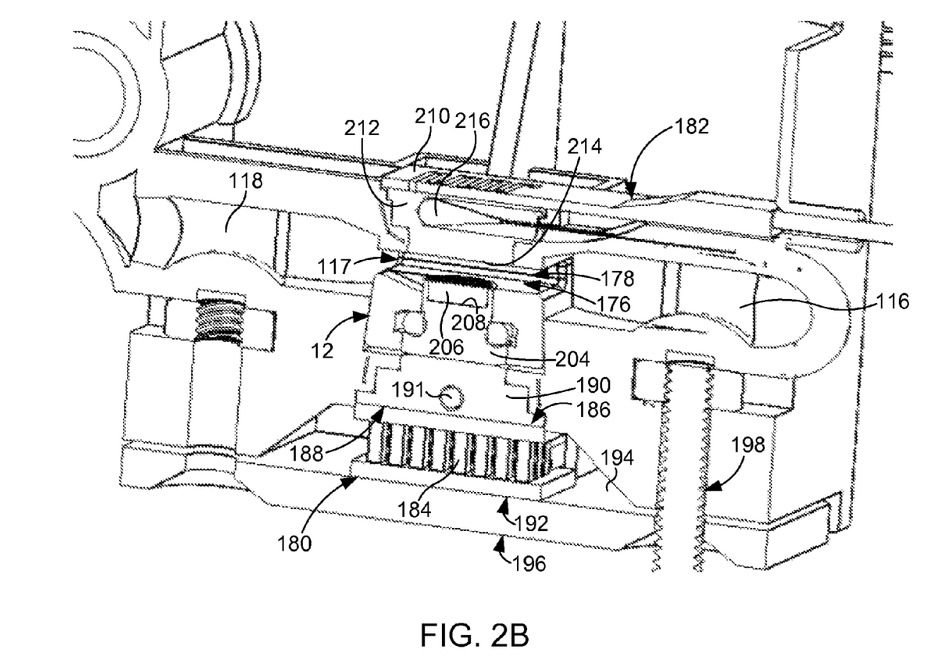

FIG. 2A shows a cross section of the sample chamber housing 96 in which the sample cartridge 12 has been removed and FIG. 2B shows a cross section of the sample chamber housing 96 in which the sample cartridge 12 is fully inserted. As shown in FIG. 2A, the sample chamber housing 96 includes a sample cartridge channel 52 configured to receive the first portion 54 of the sample cartridge 12. The sample cartridge channel 52 includes a stopping surface 150 that engages a front surface 152 of the sample cartridge (see FIG. 1D) when the sample cartridge 12 is fully inserted. The cartridge channel 52 further includes two opposed side surfaces 154 and 156 that are arranged to slideably engage two corresponding side surfaces 158 and 160 of the sample cartridge 12, respectively, as well as a lower surface 162 configured to slideably engage a lower surface 164 of the sample cartridge 12. An upper surface 166 (shown in FIG. 1C) of the cartridge channel 52 is configured to slideably receive an upper surface 168 of the sample cartridge 12.

As shown in FIG. 2A, an upper chamber boundary 170 corresponds to the notch 15 defined in the first portion 54 of the sample cartridge 12 such that, when the sample cartridge 12 is fully inserted into the cartridge channel 52, the sample chamber 117 is provided. The sample chamber 117 includes a void bounded, above, by the upper chamber boundary 170, and, below, by the internal surfaces 55 and 57 of the notch 15. The sample chamber 117 forms a portion of a flow of air through the sampler 1 within which thermophoresis is induced, thereby facilitating deposition of nanoparticles on the substrate 13. According to embodiments, the size and shape of the sample chamber 117 can be varied by varying the size and shape of the notch 15. In the illustrated embodiment, for example, the notch 15 is shown as having a rectangular shape, although other shapes such as ovular shapes, pentagonal shapes, and the like can be utilized in embodiments. Additionally, in embodiments, the internal surfaces 55 and 57 of the notch 15 can include any number of different features such as, for example, grooves, ramps, recesses, and the like.

For instance, in embodiments, a recess 172 can be defined in the lower internal surface 55 of the notch 15 to enable a user to grasp the substrate 13 with forceps. According to embodiments, by varying the design of the notch 15, characteristics of air flow and nanoparticle collection associated with a sampler assembly 10 can be varied using a number of different sample cartridges 12.

According to embodiments, nanoparticle samples are collected on a collection surface 174 of the substrate 13, which is exposed to a first region 176 (e.g., "cold" region) of the sample chamber 117. During sampling, air enters the sample chamber 117 through the first internal duct 116, passes through the sample chamber 117 and exits the sample chamber 117 into a second internal duct 118. Thermophoresis is induced in the air within the sample chamber 117 by maintaining the substrate 13 at a temperature that is lower than a temperature of a second ("warm") region 178 of the sample chamber 117. The lower temperature of the substrate 13 is achieved using a cooling mechanism 180. In embodiments, the "warm" region 178 is heated using a heating mechanism 182, while in other embodiments, the "warm" region 178 has an ambient temperature with respect to which the substrate 13 is cooled. In the embodiments illustrated in FIGS. 2A and 2B, a heating mechanism 182 is used to apply heat to the "warm" region 178. According to embodiments, the temperature difference is regulated, using the controller 92, such that thermophoresis causes nanoparticles to move toward, and be deposited on, the substrate 13.

In embodiments, the cooling mechanism 180 includes a thermoelectric cooler 184 that is thermally coupled to the substrate 13. As discussed herein, two objects are "thermally coupled" when heat can transfer from one object to the other. For example, two thermally conductive objects can be thermally coupled by placing a surface of one object in physical contact with a surface of the other object. Additionally, for example, a first object can be thermally coupled to a second object by placing a third, thermally conductive, object between the first and second objects such that a surface of each of the first and second objects contacts a surface of the third object. Similarly, a first object and a second object can be thermally coupled even though a number of objects are disposed between them, so long as contacts are made between successive objects such that heat can be conducted from the first object to the second object, or vice versa. In embodiments, thermal coupling can be achieved by ensuring good physical contact between successive objects in a thermally conductive "stack" of such objects. Physical contact can be achieved between thermally conductive objects in any number of ways such as, for example, by applying pressure to the objects, fastening the objects together, and the like.

In the illustrated embodiment, the thermoelectric cooler 184 includes a first surface 186 that contacts a first surface 188 of a thermal conduction element 190 such that the thermoelectric cooler 184 can remove heat from the thermal conduction element 190. In embodiments, a temperature sensor 191 such as, for example a thermistor, is disposed within the first thermal conduction element 190 for monitoring the temperature thereof. In other embodiments, the temperature sensor 191 can be exposed to the sample chamber 117, disposed in the sample cartridge 12, or the like. In embodiments, temperature measurements can be received from the temperature sensor 191 by the controller 92 to facilitate regulation of temperature differentials.

Figure 2C:
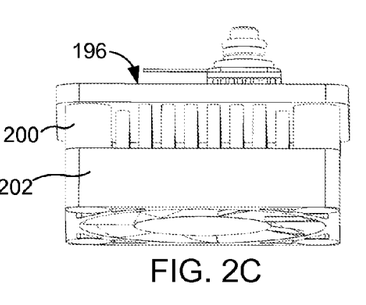
FIG. 2C is a perspective view of a cooling mechanism in accordance with embodiments of the disclosure.

The thermoelectric cooler 184 includes a second surface 192 that contacts a surface 194 of a heat dissipation mechanism 196, which, in embodiments, can include, or be integral with, the lower wall 108 of the sample chamber housing 96. In embodiments, the heat dissipation mechanism 196 removes heat from the thermoelectric cooler 184 to facilitate its operation. In embodiments, the thermoelectric cooler 184 and the thermal conduction element 190 can be held in contact, thereby facilitating thermal coupling, using a compression fastening mechanism 198 such as, for example, a combination of screws and compression springs, which may also hold the lower wall 108 of the sample chamber housing 96 in contact with the second surface 192 of the thermoelectric cooler 184. In embodiments, the heat dissipation mechanism 196 can include a thermally conductive material. For example, in some embodiments, the lower wall 108 can be integrated with other portions of the sample chamber housing 96, the sample core assembly housing 14, or the like, to further dissipate heat that is removed from the thermoelectric cooler 184. In some embodiments, as shown in FIG. 2C, the heat dissipation mechanism 196 can include a heat sink 200 and/or a fan 202 to further facilitate dissipation of heat.

As shown in FIG. 2B, a second thermal conduction element 204 is disposed within the first portion 54 of the sample cartridge 12. In embodiments, the second thermal conduction element 204 can be disposed within the sample chamber housing 96. In some embodiments, one thermal conduction element may be used, while, in other embodiments, two or more thermal conduction elements may be used. In the illustrated embodiments, thermal coupling is maintained between the thermoelectric cooler 184 and the first thermal conduction element 190, between the first and second thermal conduction elements 190 and 204, and between the second thermal conduction element 204 and the substrate 13. By maintaining physical contact between these elements, the thermoelectric cooler 184 can be thermally coupled to the substrate 13 and, thus, can remove heat from the substrate 13, thereby cooling the substrate 13 to maintain the temperature difference within the sample chamber 117. In the illustrated embodiment, a magnet 206 disposed on an upper surface 208 of the second thermal conduction element 204 holds a magnetic nanoparticle collection substrate 13 in place, and thermal coupling is also maintained between the substrate 13, the magnet 206, and the second thermal conduction element 204. In other embodiments, a non-magnetic substrate may be held in place using another means such as, for example, a mechanical means, in which case a magnet 206 may not be present and the upper surface 208 of the second thermal conduction element 204 can be held in contact with the substrate 13.

In the illustrated embodiment, the heating mechanism 182 includes a heating element 210 such as, for example, a resistive heater, that applies heat to a thermal conduction element 212 that is disposed in the sample chamber housing 96. A lower surface 214 of the thermal conduction element 212 can be exposed to the second region 178 of the sample chamber 117 and the heating element is thermally coupled to the thermal conduction element 212 to facilitate raising the temperature of the second ("warm") region 178. In embodiments, a temperature sensor 216 such as, for example a thermistor, can be disposed within the thermal conduction element 212 to monitor the temperature thereof. In other embodiments, the temperature sensor 216 can be exposed to the sample chamber 117, disposed in the sample cartridge 12, or the like. In embodiments, temperature measurements can be received from the temperature sensor 216 by the controller 92 to facilitate regulation of temperature differentials.

Figure 3A:
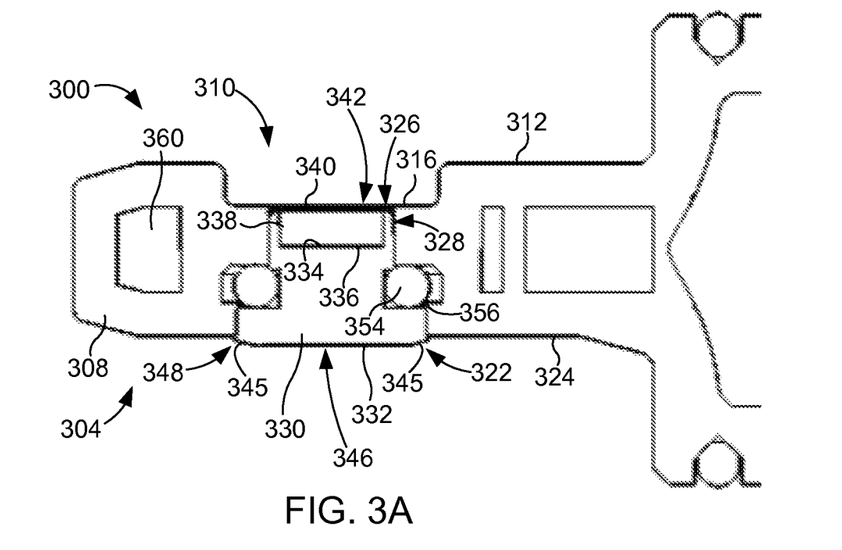
FIG. 3A is a cross-sectional side view of a sample cartridge in accordance with embodiments of the disclosure.
Figure 3B:
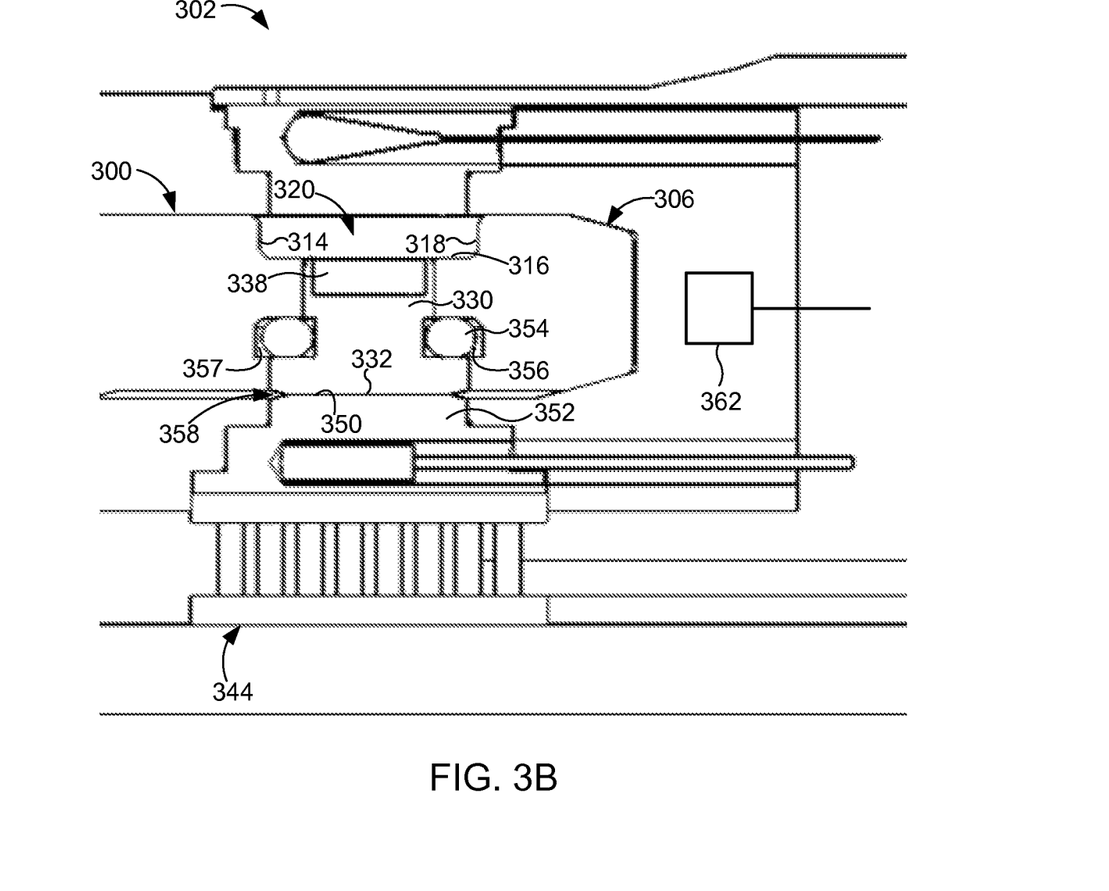
FIG. 3B is a cross-sectional side view of a sample chamber housing in accordance with embodiments of the disclosure.
Figure 4A:
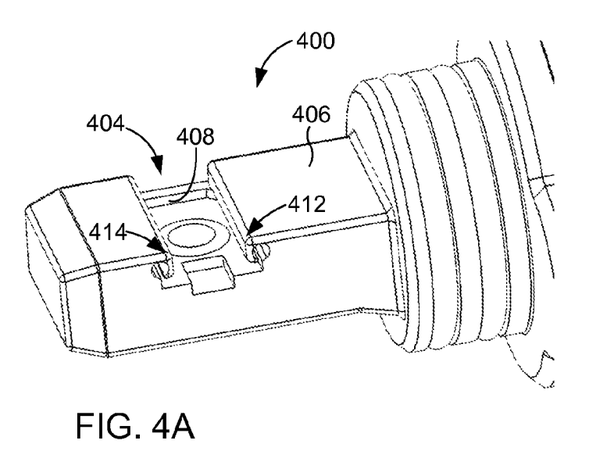
FIGS. 4A-4C are perspective views of a sample cartridge in accordance with embodiments of the disclosure.
Figure 4B:
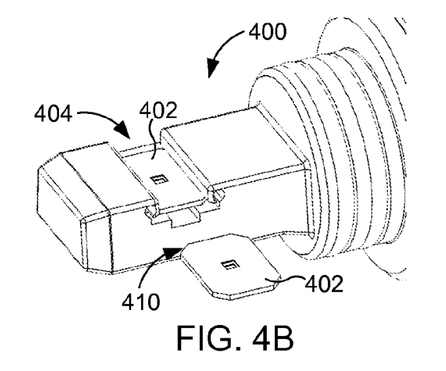
Figure 4C:
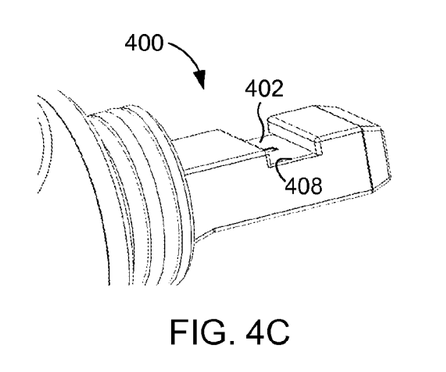
Figure 4D:
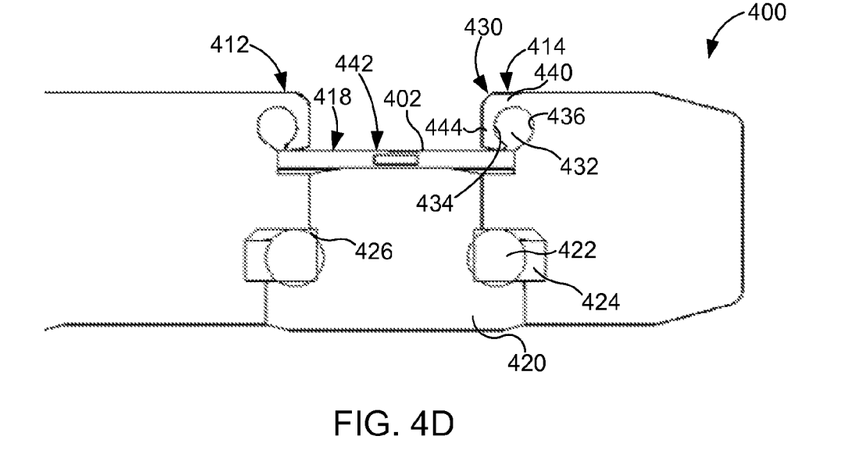
FIG. 4D is a a cross-sectional side view of a sample cartridge in accordance with embodiments of the disclosure.

FIGS. 3A and 3B depict a cross-sectional side view of an illustrative sample cartridge 300 and a sample chamber housing 302 having the cartridge 300 fully inserted, in accordance with embodiments of the disclosed subject matter. In embodiments, the sample cartridge 300 includes a first portion 304 configured to fit within a cartridge channel 306. As shown, the first portion 304 includes a body 308 having a notch 310 defined in an upper wall 312. In embodiments, as shown, for example, in FIG. 3B, internal surfaces 314, 316, and 318 of the notch 310 define a portion of the sample chamber 320 when the cartridge 300 is fully inserted into the cartridge channel 306.

In embodiments, the first portion 304 of the cartridge 300 has an opening 322 defined in the bottom surface 324, an opening 326 defined in the internal surface 316 of the notch 310 and a hollow channel 328 extending between the two openings 322 and 326. A first thermal conduction element 330 is disposed within the channel 328 such that a lower surface 332 of the first thermal conduction element 330 extends from the opening 322 and an upper surface 334 of the first thermal conduction element 330 contacts a lower surface 336 of a thermally conductive magnet 338. The magnet 338 is configured to hold a magnetic substrate 340, which is disposed within the opening 326. An upper surface 342 of the substrate 340 is used as a collection surface and the first thermal conduction element 330, the magnet 338, and the substrate 340 are all thermally coupled.

According to embodiments, to facilitate sealing the sample chamber from the ambient environment such that air only enters the sample chamber through the air flow path, the sample cartridge 300 is configured to fit snugly within the cartridge channel 306. In embodiments, to further facilitate this seal, as well as to facilitate thermal coupling between a cooling mechanism 344 and the substrate 340, the lower surface 332 of the first thermal conduction element 330 includes an angled feature 345 such that an interior portion 346 of the lower surface 332 extends downward farther than the periphery 348. For example, as shown in FIGS. 3A and 3B, the angled feature 345 can include a beveled edge extending annularly around the periphery 348 of the lower surface 332 of the first thermal conduction element 330. When the cartridge 300 is inserted into the cartridge channel 306, the angled feature 345 engages an upper surface 350 of a second thermal conduction element 352, causing an upward force on the thermal conduction element 330. An elastic mechanism 354 (e.g., a spring, an elastomeric o-ring, or the like), partially disposed within a recess 356 defined in the cartridge 300 and partially disposed within a recess 357 defined within the first thermal conduction element 330, compresses in response to the upward force, thereby facilitating contact between the second thermal conduction element 352, the first thermal conduction element 330, the magnet 338, and the substrate 340, which, in embodiments, enables thermal coupling between the second thermal conduction element 352 and the substrate 340. According to embodiments, the upper surface 350 of the second thermal conduction element 352 may also include an angled feature 358.

According to embodiments of the disclosed subject matter, the cartridge 300 may include one or more communication components. For example, in embodiments, the cartridge 300 may include a radio-frequency identification (RFID) tag 360 that can be read by an RFID sensor 362 disposed in the sample chamber housing 302. In embodiments, other types of wired or wireless communication components can be integrated with the cartridge 300 and/or the sampler assembly such as, for example, USB components, BLUETOOTH® components, or the like. Communications between the cartridge 300 and the sampler assembly can be used to transfer information related to users, samples, sample processes, instructions for sampling, ambient condition measurements, and the like.

FIGS. 4A-4D show another illustrative sample cartridge 400 in accordance with embodiments of the disclosed subject matter. The illustrative cartridge 400 retains a substrate 402 mechanically. Thus, for example, in embodiments, the illustrative cartridge 400 can be used to hold substrates 402 that do not include magnetic material. As shown, the cartridge 400 includes a notch 404 defined in an upper surface 406. A retaining wall 408 is disposed within the notch 404 and is configured to engage at least a portion of a periphery 410 of the substrate 402. In embodiments, the retaining wall 408 has a shape that corresponds to the shape of the outside periphery 410 of the substrate 402. A first deflection feature 412 is provided on a first side of the notch 404 and a second deflection feature 414 is provided on a second side of the notch 404. The deflection features 412 and 414 provide a force on an upper surface 418 of the substrate 402, thereby causing a downward force on the substrate 402. When the cartridge 400 is fully inserted into a sampler assembly, this downward force opposes the upward force on a thermal conduction element 420 (described, for example, above), thereby facilitating thermal coupling between the thermal conduction element 420 and the substrate 402. An elastic mechanism 422 (e.g., a spring, an elastomeric o-ring, or the like) is disposed partially within a recess 424 defined within the cartridge 400 and partially within a recess 426 defined within the thermal conduction element 420, and can, in embodiments, facilitate thermal coupling of the thermal conduction element 420 and the substrate 402. Additionally, in embodiments, the configuration of the deflection features 412 and 414 enables a user to slide the substrate 402 into, and out of, engagement with the cartridge 400.

In the illustrated embodiments, each deflection feature 412 and 414 includes an arm 430 that curves (or otherwise turns), thereby defining a void 432 between an inside surface 434 of the arm 430 and an inside surface 436 of the notch 404. The arm 430 includes a first portion 440 extending toward the center 442 of the substrate 402 with a generally parallel orientation with respect to the upper surface 418 of the substrate 402. The arm 430 includes a second portion 444 extending toward the upper surface 418 with a generally perpendicular orientation with respect to the upper surface 418 of the substrate 402. A tab 446 extends from the end of the second portion 444 at least partially away from the center 442 of the substrate 402 and engages the upper surface 418 of the substrate 402, as shown, for example, in FIG. 4D. In embodiments, the deflection features 412 and 414 can be created by boring a hole (e.g., the void 432) near the top of each inside surface 436 of the notch 404. In other embodiments, the deflection features 412 and 414 can be created during a molding process for creating the cartridge 400. Additionally, according to embodiments, the deflection features 412 and 414 can include any number of different configurations suitable for engaging a portion of a substrate 404 and providing a force on the substrate 404 that facilitates maintenance of thermal coupling between the substrate 404 and the thermal conduction element 420.

According to embodiments, a miniature thermophoretic sampler can be designed to be coupled upstream of an active sampling aerosol monitor to collect aerosol (e.g., nanoparticles, gases and other airborne particulate matter) for subsequent physical and chemical analyses. In embodiments, the sampler collects airborne nanoparticles onto a substrate while providing minimal interference with a downstream, active-sampling aerosol monitor so that, for example, a real-time continuous monitor may also capture a time-integrated sample for subsequent laboratory characterization and analysis. Analysis of samples collected by embodiments of the sampler may provide forensic information on the sampled aerosol (e.g., size distribution, shape, chemical and physical composition of particles). In embodiments, the thermophoretic sampler uses thermophoretic force to collect a small percentage (e.g., less than 5%) of the sampled aerosol onto a substrate, while the remainder of the sampled aerosol flows into an active monitor, gas monitor, biosensor, or the like.

Figures 5A, 5B, 5C, 5D:
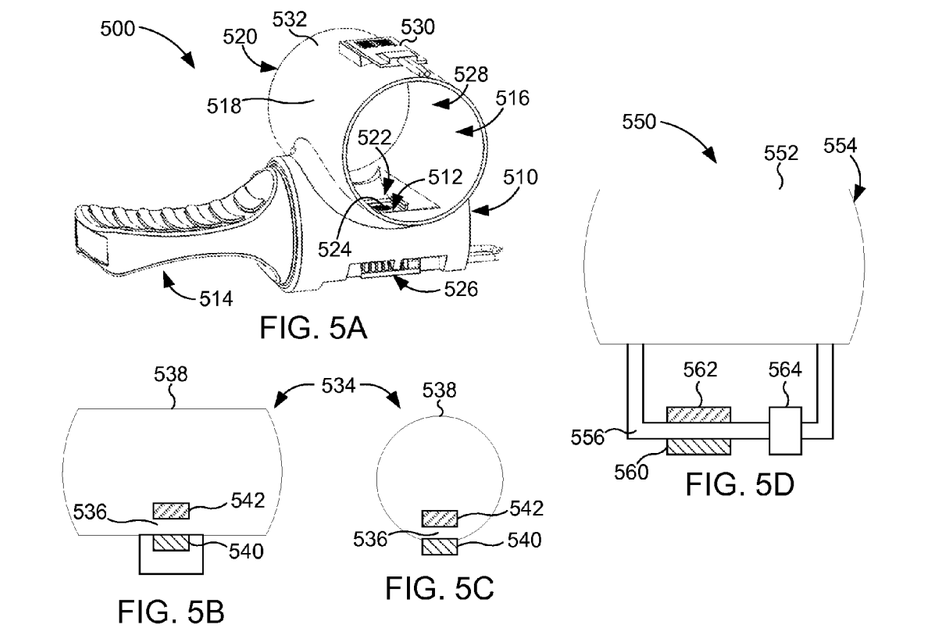
FIG. 5A is a perspective view of a thermophoretic sampler in accordance with embodiments of the disclosure.
FIGS. 5B-5D are schematic diagrams depicting thermophoretic samplers in accordance with embodiments of the disclosure.

FIG. 5A shows an illustrative thermophoretic sampler 500 that is configured for attachment to a device such as, for example, active sampling aerosol monitor, in accordance with embodiments of the disclosed subject matter. As shown, the sampler 500 includes a sample chamber housing 510 that includes a cartridge channel 512 configured to receive a sample cartridge 514. In embodiments, the cartridge channel 512 and sample cartridge 514 can be similar to the cartridge channel 52 and the sample cartridge 12 described above with reference, for example, to FIGS. 1A, 1C, 1D, and the cartridge channel 306 and cartridge 300 described above with reference to FIGS. 3A and 3B. In the illustrated embodiments, the sample chamber housing 510 includes a sample chamber 516 partially defined by a tube portion 518. In embodiments, an end 520 of the tube portion 518 can be adapted to be removably coupled to an inlet of an air intake device (not shown) that may be used, for example, to collect aerosol samples, analyze aerosol samples, and the like. According to embodiments, the sampler 500 can be used as an upstream nanoparticle sampler in conjunction with other types of particle collectors, samplers, and/or analyzers.

As shown in FIG. 5A, the tube portion 518 includes an aperture 522 through which a substrate 524 is exposed to the sample chamber 516. A cooling mechanism 526 can be thermally coupled to the substrate 524 to facilitate reducing the temperature of the substrate 524 below a temperature of a "warm" region 528 of the sample chamber 516. In embodiments, the cooling mechanism 526 can be similar to cooling mechanisms described herein with reference to other embodiments of the disclosed subject matter. In embodiments, a heating mechanism 530 can be disposed on an upper surface 532 of the tube portion 518 to facilitate introducing heat to the "warm" region 528.

FIGS. 5B and 5C are schematic diagrams depicting other embodiments of a sampler 534 in which a sample chamber 536 that is smaller than the tube portion 538 is defined by placement of a cooling mechanism 540 and a heating mechanism 542. For example, in embodiments, the cooling mechanism 540 can be disposed below the tube portion 538, and the heating mechanism 542 can be disposed a desired distance above the cooling mechanism 540, within the tube portion 538. In embodiments, the positions of the cooling mechanism 540 and/or the heating mechanism 542 can be adjustable.

FIG. 5D is a schematic diagram depicting another embodiment of a thermophoretic sampler 550 that can be used in conjunction with other devices. As shown in FIG. 5B, the sampler 550 includes a tube portion 552 having an end 554 adapted for coupling to another device (not shown). In the illustrated embodiment, a sampling chamber 556 is provided in a secondary flow path 558. According to embodiments, a cooling mechanism 560 and/or a heating mechanism 562 can be used to induce thermophoresis within the sampling chamber 556. In embodiments, the secondary flow path 558 can be passive such that a portion of air flowing through the tube portion 552 is naturally diverted into the secondary flow path 558. In other embodiments, the secondary flow path 558 includes a pump 564 that pulls air into the secondary flow path 558.

Figure 5E:
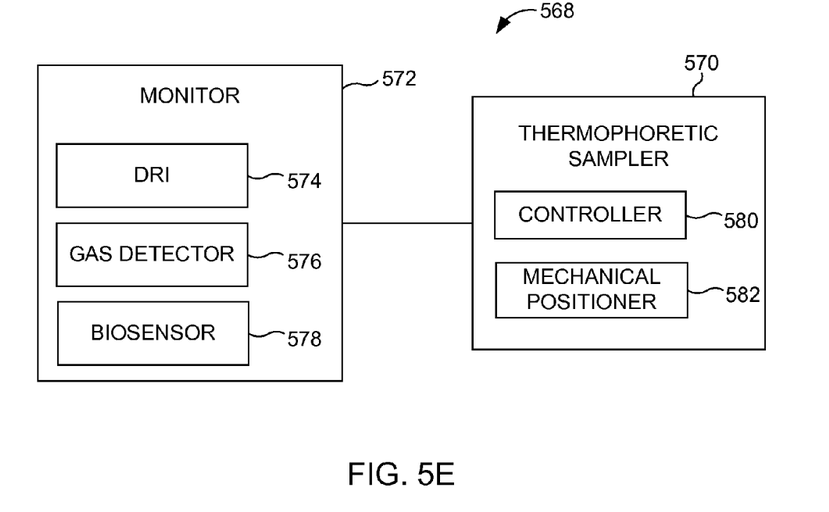
FIG. 5E is a schematic diagram depicting a thermophoretic sampler coupled to an active monitor in accordance with embodiments of the disclosure.

FIG. 5E is a schematic diagram depicting an illustrative operating environment 568 in which a thermophoretic sampler 570 is coupled to an active sampling aerosol monitor 572, in accordance with embodiments of the disclosed subject matter. The illustrative operating environment 568 shown in FIG. 5E is not intended to suggest any limitation as to the scope of use or functionality of embodiments of the subject matter disclosed throughout this document. Neither should the illustrative operating environment 568 be interpreted as having any dependency or requirement related to any single component or combination of components illustrated therein. For example, in embodiments, the illustrative operating environment 568 can include additional components such as, for example components of an active particle monitor 572, activity sensors (e.g., accelerometers), and the like. Additionally, any one or more of the components depicted in FIG. 5E can be, in embodiments, integrated with various ones of the other components depicted therein (and/or components not illustrated).

According to embodiments, the active sampling aerosol monitor 572 may be, or include, monitors such as, for example, a direct reading instrument (DRI) 574, a gas detector 576, a biosensor 578, and/or the like. In embodiments, a monitor 572 (or component thereof) may be used to trigger (e.g., via communication with a controller 580) or control the thermophoretic sampler 570. In embodiments, the position of the substrate (not shown) can be controlled using a mechanical positioner 582, which may be triggered and/or controlled by either the thermophoretic sampler 570 or one or more monitors. For example, in embodiments, a DRI 574 may trigger the thermophoretic sampler 570 to begin collecting nanoparticles onto an appropriate substrate in response to sensing a spike in nanoparticle concentration level. As another example, in embodiments, a gas detector 576 may trigger the thermophoretic sampler 570 to begin collecting nanoparticles onto an appropriate substrate in response to sensing a specific gas concentration level. As another example, in embodiments, a biosensor 578 may trigger the thermophoretic sampler to begin collecting nanoparticles onto an appropriate substrate in response to detecting a specific biogen concentration level.

Figure 6:
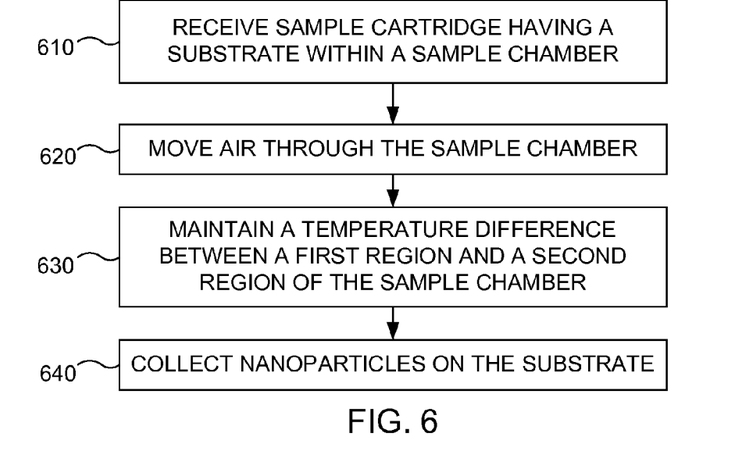
FIG. 6 is a flow diagram depicting an illustrative method of collecting nanoparticles in accordance with embodiments of the disclosure.

FIG. 6 is a flow diagram depicting an illustrative method for collecting nanoparticles in accordance with embodiments of the disclosed subject matter. According to embodiments of the illustrative method, a sample chamber receives a sample cartridge having a substrate disposed thereon (block 610). Air is moved through the sample chamber (block 620) and a controller is used to maintain a temperature difference between a first region and a second region of the sample chamber, thereby inducing thermophoresis (block 630). Due to the thermophoresis, nanoparticles are collected on the substrate (block 640).

Figure 7:
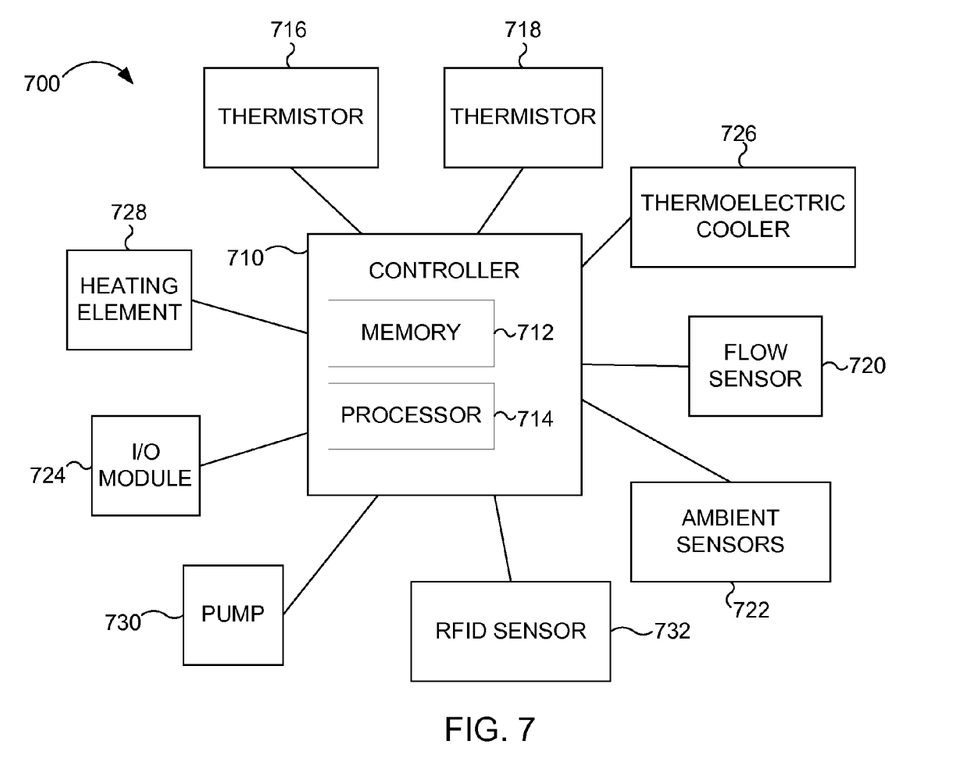
FIG. 7 is a block diagram illustrating an operating environment in accordance with embodiments of the disclosure.

FIG. 7 depicts an illustrative operating environment 700 associated with a personal thermophoretic sample such as, for example, the illustrative sampler 1, depicted in FIGS. 1A-1H. The illustrative operating environment 700 includes a controller 710 that facilitates various aspects of operations described herein. For example, in embodiments, the controller 710 can maintain a temperature difference between the substrate and a "warm" region of the sample chamber, control the pump, and the like. According to embodiments, the controller can include a one or more memory components 712 and one or more processors 714. In embodiments, the controller 710 can receive information from a number of different sources, can store information in the memory component 712 and can use the processor(s) 714, for example, to execute computer-executable instructions (which may be stored in the memory component 712) that cause the controller to perform any number of different processes, methods, actions, and the like. For example, in embodiments, the controller 710 receives temperature measurements from one or more thermistors 716 and 718, air flow measurements from a flow sensor 720, measurements of ambient conditions (e.g., ambient temperature, ambient air pressure, ambient relative humidity) from ambient sensors 722, input from a user via an input/output (I/O) module 724, and the like, and can use some or all of the received information to perform algorithms that facilitate aspects of functionality described herein.

In embodiments, the controller 710 creates a thermophoretic temperature differential between two regions of a sample chamber using a thermoelectric cooler 726 and, in embodiments, a heating element 728 (e.g., a resistive heater). In embodiments, for example, heat flow can be regulated using proportional-integral-differential (PID) control software that feeds back into the thermoelectric cooler 726 and heating element 728. Air flow can be monitored using flow measurements received from the flow sensor 720 and can be controlled using a pump 730. According to embodiments, the controller 710 can utilize any number of different control algorithms, servos, hardware, firmware, and the like, to maintain temperature differentials, time sampling procedures, regulate air flow, and the like. In embodiments, for example, a programmable logic device can be used as a safety shut-off in case of temperature fault.

Additionally, as depicted in FIG. 7, the controller 710 can communicate with a radio frequency identification (RFID) sensor 732 or other communication module. In embodiments, other types of communication modules can be used such as, for example, wireless communication modules, wired communication modules, and the like. For example, in an embodiment, the RFID sensor 732 can receive information from an RFID tag associated with a sample cartridge. In embodiments, the RFID tag can include information identifying a user, information identifying a particular sampling procedure to be followed, or the like. In embodiments, the RFID sensor 732 can be configured to receive information from an RFID tag attached by a person, disposed in a doorframe, located at a workstation, or the like, such that the controller 710 can obtain information associated with a particular environment, user, or the like.

The illustrative operating environment 700 shown in FIG. 7 is not intended to suggest any limitation as to the scope of use or functionality of embodiments of the invention disclosed throughout this document. Neither should the illustrative operating environment 700 be interpreted as having any dependency or requirement related to any single component or combination of components illustrated therein. For example, in embodiments, the illustrative operating environment 700 can include additional components such as, for example components of an active particle monitor, activity sensors (e.g., accelerometers), and the like. Additionally, any one or more of the components depicted in FIG. 7 can be, in embodiments, integrated with various ones of the other components depicted therein (and/or components not illustrated). Any number of other components or combinations of components can be integrated with the illustrative operating environment 700 depicted in FIG. 7, all of which are considered to be within the scope of this disclosure.

Embodiments of the disclosed subject matter are described in the general context of computer-executable instructions. Computer-executable instructions can include, for example, computer code, machine-useable instructions, and the like such as, for example, program components, capable of being executed by one or more processors associated with a computing device. Generally, program components including routines, programs, objects, modules, data structures, portions of one or more of the preceding, and the like, refer to code that, when executed, causes a computing device (e.g., a processor) to perform particular tasks (e.g., methods, calculations, etc.) or implement or manipulate various abstract data types. Some or all of the functionality contemplated herein can also be implemented in hardware, firmware, or a combination of software, hardware, and/or firmware.

In embodiments, the memory component 712 can include computer-readable media. Computer-readable media include both volatile and non-volatile media, removable and nonremovable media, and contemplate media readable by a database, a processor, a router, and various other networked devices. By way of example, and not limitation, computer-readable media can include media implemented in any method or technology for storing information. Examples of stored information include computer-executable instructions, data structures, program modules, and other data representations. Media examples include, but are not limited to, Random Access Memory (RAM); Read Only Memory (ROM); Electronically Erasable Programmable Read Only Memory (EEPROM); flash memory or other memory technologies; Compact Disc Read-Only Memory (CD-ROM), digital versatile disks (DVDs) or other optical or holographic media; magnetic cassettes, magnetic tape, magnetic disk storage or other magnetic storage devices; data transmissions; or any other medium that can be used to encode information and can be accessed by a computing device such as, for example, quantum state memory, and the like.

According to embodiments, various components of the operating environment 700 can be implemented on one or more computing devices that are communicatively coupled to the thermophoretic sampler. According to embodiments, the computing device can include any type of computing device suitable for implementing embodiments of the invention. Examples of computing devices include "processors," "controllers," "workstations," "servers," "laptops," "desktops," "tablet computers," "hand-held devices," and the like, all of which are contemplated within the scope of FIG. 7 and reference to various components of the operating environment 700. In embodiments, components of the operating environment 700 can include more than one computing device such as, for example, in a distributing computing environment, a networked environment, and the like. For example, in embodiments, portions of the components of the operating environment 700 can be hosted on a computing device in the sampler 1, while other portions can be hosted on a handheld device, laptop, or other computing device.

In embodiments, a computing device includes a bus that, directly and/or indirectly, couples the following devices: a processor, a memory, an input/output (I/O) port, an I/O component, and a power supply. Any number of additional components, different components, and/or combinations of components can also be included in the computing device. The bus represents what may be one or more busses (such as, for example, an address bus, data bus, or combination thereof). Similarly, in embodiments, the computing device can include a number of processors, a number of memory components, a number of I/O ports, a number of I/O components, and/or a number of power supplies. According to embodiments, the processor (or processors) reads data from various entities such as a memory component, user interface, or sensors.

While the subject matter of embodiments of the disclosure is described with specificity, the description itself is not intended to limit the scope of this patent. Rather, the inventors have contemplated that the claimed subject matter might also be embodied in other ways, to include different steps or features, or combinations of steps or features similar to the ones described in this document, in conjunction with other technologies. For example, in embodiments, a number of substrates can be coupled to a moveable (e.g., slidable, rotatable, or the like) substrate holder that moves each substrate into a position in which it is exposed to the sample chamber in succession, thereby facilitating nanoparticle collection in a controllable time series. Additionally, in embodiments, for example, a thermophoretic sampler may include an impactor that can be used to limit the size of particles entering the sample chamber. Moreover, although the term "block" may be used herein to connote different elements of methods or algorithms employed, the term should not be interpreted as implying any particular order among or between various steps herein disclosed unless and except when the order of individual steps is explicitly called for.

The following is claimed:

1. A thermophoretic sampling device, the device comprising:
    a sample chamber housing, comprising:
        a sample chamber defined within the sample chamber housing, the sample chamber defining a portion of a flow path for air;
        a cartridge channel defined within the sample chamber housing; and
        a thermoelectric cooler;
    a sample cartridge configured to be removably inserted into the cartridge channel, the sample cartridge comprising:
        a substrate having a collection surface configured to be exposed to a first region of the sample chamber in response to the sample cartridge being inserted into the cartridge channel; and
        a first thermal conduction element that is thermally coupled to the substrate, where the first thermal conduction element is configured to be thermally coupled to the thermoelectric cooler in response to the sample cartridge being inserted into the cartridge channel;
    a sample core assembly, wherein the sample chamber housing is defined within the sample core assembly; and
    a cartridge port, the cartridge port comprising an opening defined in an outside surface of the sample core assembly;
    wherein the cartridge channel extends from the cartridge port to the sample chamber; and
    wherein the sample cartridge is configured to be removably inserted into the cartridge channel through the cartridge port.

2. The device of claim 1, wherein the thermoelectric cooler comprises a first surface and a second surface, wherein the first surface of the thermoelectric cooler is configured to contact a first surface of the first thermal conduction element and, wherein the second surface of the thermoelectric cooler contacts a heat dispersion mechanism.

3. The device of claim 2, the heat dispersion mechanism comprising at least one of a thermally conductive housing and a heat sink.

4. The device of claim 1, further comprising:
    a second thermal conduction element having a first surface and a second surface, wherein the first surface of the second thermal conduction element is exposed to a second region of the sample chamber; and
    a heating element having a surface that contacts the second surface of the second thermal conduction element.

5. The device of claim 1, wherein at least a portion of the sample chamber is bounded by an inside surface of a tube portion, wherein a first end of the tube portion is adapted to be coupled to an inlet of an active sampling aerosol monitor.

6. The device of claim 1, the sample cartridge comprising:
    a first portion configured to fit within the cartridge channel, wherein the first thermal conduction element is disposed within the first portion and, wherein the substrate is removably coupled to the first portion;
    a second portion configured to be gripped to facilitate insertion and removal of the sample cartridge; and
    a third portion disposed between the first portion and the second portion, wherein the third portion includes a sealing mechanism.

7. The device of claim 6, the first portion of the cartridge comprising:
    a bottom surface, wherein a first opening is defined in the bottom surface;
    an upper surface, wherein a notch is defined in the upper surface;
    a second opening, wherein the second opening is defined in an inside surface of the notch; and
    a hollow channel extending from the first opening to the second opening, wherein the first thermal conduction element is disposed within the hollow channel such that the surface of the first thermal conduction element extends from the first opening.

8. The device of claim 7, wherein the surface of the first thermal conduction element includes an angled feature that facilitates application of an upward force on the surface when the first portion of the cartridge is inserted into the cartridge channel, and wherein the upward force causes compression of an elastic mechanism disposed within the hollow channel, thereby facilitating thermal coupling between the substrate and the first thermal conduction element.

9. The device of claim 7, the upper surface of the first portion of the cartridge further comprising a deflection feature that engages a periphery of the substrate.

10. A system for collecting nanoparticles on a substrate, the system comprising:
    a sample core assembly having a sample chamber defined therein, the sample core assembly comprising: (1) an opening defined in an outside wall of the sample core assembly, (2) a cooling mechanism, and (3) a cartridge channel extending from the opening to the sample chamber;
    a sample cartridge configured to be removably inserted into the cartridge channel through the opening;
    a substrate removably coupled to the sample cartridge, wherein the cooling mechanism is configured to be thermally coupled to the substrate in response to the sample cartridge being inserted into the cartridge channel; and
    a controller that controls the cooling mechanism to maintain the substrate at a temperature that is lower than a temperature of a warm region of the sample chamber, thereby inducing thermophoresis.

11. The system of claim 10, further comprising a heating element that applies heat to the warm region of the sample chamber.

12. The system of claim 10, further comprising an air flow mechanism, the air flow mechanism comprising:
    a pump that pulls air into the sample core assembly through an air inlet; and
    a flow sensor that determines an amount of air being moved through the sample core assembly.

13. The system of claim 10, wherein the sample cartridge comprises a radio-frequency identification (RFID) tag and, wherein the sample core assembly comprises an RFID sensor that obtains information from the RFID tag.

14. The system of claim 10, further comprising an ambient sensor that measures at least one of an ambient temperature, an ambient air pressure, and an ambient relative humidity.

* * * * *